(12) United States Patent
Castella et al.

(10) Patent No.: US 8,771,226 B2
(45) Date of Patent: Jul. 8, 2014

(54) VENA CAVA FILTER CATHETER AND METHOD

(75) Inventors: Paul Castella, San Antonio, TX (US); Jeffrey N. Steinmetz, Arvada, CO (US)

(73) Assignee: Bio2Medical, Inc., San Antonio, TX (US)

(*) Notice: Subject to any disclaimer, the term of this patent is extended or adjusted under 35 U.S.C. 154(b) by 333 days.

(21) Appl. No.: 13/031,037

(22) Filed: Feb. 18, 2011

(65) Prior Publication Data

US 2011/0208134 A1    Aug. 25, 2011

Related U.S. Application Data

(60) Provisional application No. 61/305,872, filed on Feb. 18, 2010.

(51) Int. Cl.
*A61M 29/00* (2006.01)

(52) U.S. Cl.
USPC ........... 604/105; 604/509; 604/508; 604/507; 604/266; 606/200

(58) Field of Classification Search
USPC ................. 604/104–107, 266, 108, 109, 500, 604/507–509; 606/200
See application file for complete search history.

(56) References Cited

U.S. PATENT DOCUMENTS

| | | | |
|---|---|---|---|
| 4,714,460 A | 12/1987 | Calderon | 604/28 |
| 4,832,055 A * | 5/1989 | Palestrant | 128/899 |
| 4,867,742 A | 9/1989 | Calderon | 604/1 |
| 5,149,330 A | 9/1992 | Brightbill | 604/280 |
| 5,167,623 A | 12/1992 | Cianci et al. | 604/43 |
| 5,217,484 A * | 6/1993 | Marks | 606/200 |
| 5,810,789 A | 9/1998 | Powers et al. | 604/280 |
| 6,113,576 A | 9/2000 | Dance et al. | 604/164 |
| 6,482,222 B1 | 11/2002 | Bruckheimer et al. | 606/200 |
| 6,524,302 B2 | 2/2003 | Kelley | 604/523 |
| 6,712,798 B2 | 3/2004 | Constantz | 604/284 |
| 8,252,019 B2 * | 8/2012 | Fleming, III | 606/200 |

(Continued)

FOREIGN PATENT DOCUMENTS

| | | | |
|---|---|---|---|
| WO | WO 2004/034884 | 4/2004 | |
| WO | WO 2008/010197 | 1/2008 | A61F 2/01 |
| WO | WO 2009/029681 | 3/2009 | A61M 5/00 |
| WO | WO 2011/103486 | 8/2011 | A61M 27/04 |

OTHER PUBLICATIONS

Decousus, H., et al., "A clinical trial of vena caval filters in the prevention of pulmonary embolism in patients with proximal deep-vein thrombosis." *New England Journal of Medicine* 338: 409-415 (1998).

(Continued)

*Primary Examiner* — Kami A Bosworth
(74) *Attorney, Agent, or Firm* — David G. Rosenbaum; Matthew M. Remissong; Rosenbaum IP

(57) ABSTRACT

A vena cava filter catheter includes a catheter having a lumen disposed therethrough and at least one strand of biocompatible wire. The at least one strand has a first state in which the at least one strand has an elongate geometry suitable for traversing the lumen of the catheter and a second state in which the at least one strand assumes a pre-set geometry in which the at least one strand assumes a tortuous configuration adapted to occupy a space approximating a luminal diameter of an inferior vena cava.

18 Claims, 4 Drawing Sheets

(56) References Cited

U.S. PATENT DOCUMENTS

| | | | |
|---|---|---|---|
| 2001/0031980 A1* | 10/2001 | Wensel et al. | 606/200 |
| 2001/0044634 A1* | 11/2001 | Don Michael et al. | 606/200 |
| 2004/0199202 A1* | 10/2004 | Dubrul et al. | 606/200 |
| 2005/0085765 A1 | 4/2005 | Voorhees | 604/43 |
| 2006/0047300 A1* | 3/2006 | Eidenschink | 606/200 |
| 2006/0190025 A1 | 8/2006 | Lehe et al. | 606/200 |
| 2007/0191878 A1* | 8/2007 | Segner et al. | 606/200 |
| 2008/0027481 A1* | 1/2008 | Gilson et al. | 606/200 |
| 2008/0262532 A1* | 10/2008 | Martin | 606/200 |
| 2009/0062840 A1 | 3/2009 | Angel | 606/200 |
| 2010/0217304 A1 | 8/2010 | Angel et al. | 606/200 |
| 2011/0106135 A1* | 5/2011 | Thompson et al. | 606/200 |
| 2012/0083822 A1* | 4/2012 | Anukhin et al. | 606/200 |

OTHER PUBLICATIONS

Greenfield, L., et al., "A New Intracaval Filter Permitting Continued Flow and Resolution of Emboli-Surgery" *Surgery* 4: 599-606 (1973).

Lin, P., et al., "Use of vena caval filters in the treatment of acute deep venous thrombosis." *Endovascular Today* Jan: 40-50 (2005).

Mobin-Uddin, K., et al. *JAMA* 208(2): 301-306 (1969).

PCT International Search Report from PCT international application PCT/US2011/025510, pp. 1-5 (Nov. 21, 2011).

* cited by examiner ined the inferior vena cava. Vena cava filters are typically deployed infrarenally within the inferior vena cava, but may be deployed suprarenally as well.
VENA CAVA FILTER CATHETER AND METHOD

CROSS REFERENCE TO RELATED INVENTIONS

The present application claims priority from U.S. Provisional Patent Application Ser. No. 61/305,872, filed on Feb. 18, 2010, which is hereby incorporated by reference in its entirety herein.

FIELD OF THE INVENTION

The present invention pertains generally to the field of vascular filters for capturing embolic or thrombotic material in the blood flow. More particularly, the present invention pertains generally to filter devices for capturing thrombus in the inferior vena cava which flows from the peripheral vasculature toward the lungs.

BACKGROUND OF THE INVENTION

Filter devices for capturing thrombus in the inferior vena cava, commonly referred as "vena cava filters," are typically delivered to the inferior vena cava by either a femoral or a jugular approach using a catheter to traverse the vasculature and deploy the filter. Vena cava filters are typically deployed infrarenaly within the inferior vena cava, but may be deployed suprarenaly as well.

Vena cava filters typically fall into two general classes: permanent and temporary. Permanent vena cava filters are deployed in such a manner as to engage the vascular wall of the inferior vena cava such as by embedding barbs into the tissue followed by subsequent release from the delivery catheter. Temporary vena cava filters typically are deployed and expand against, but do not permanently embed themselves in the vascular tissue, thereby facilitating removal. Temporary vena cava filters are usually released from the delivery catheter, then later retrieved by using a retrieval catheter that shares or otherwise engages the temporary vena cava filter and collapses it for withdrawal using the catheter.

The accepted standard of care for patients with venous thromboembolism (VTE) is anticoagulant therapy. Inferior vena cava (IVC) filters are reserved for those patients who fail anticoagulant therapy, or have a complication or contraindication to anticoagulant therapy. Until the early 1970's, the only method of IVC interruption was surgical, either by clipping, ligation or plication. The first clinical experience of an endoluminally-placed device to interrupt IVC flow was reported by Mobin-Uddin et al. in 1969. However, it was not until the introduction of a stainless steel umbrella-type filter by Greenfield et al. in 1973 that an effective method of endoluminally trapping emboli while simultaneously preserving IVC flow became possible. Indeed, for many years, the Greenfield filter set a benchmark by which newer filters were measured. Early generations of filters were inserted by surgical cut-down and venotomy. Eventually filters were able to be inserted percutaneously: initially through large 24 Fr sheaths, though newer generations of filters are able to be delivered through 6 Fr systems.

Despite the safety and efficacy of modern day filters, systemic anticoagulation remains the primary treatment for VTE. Either unfractionated or low molecular weight heparin followed by three months of oral anticoagulation in patients with proximal deep venous thrombosis (DVT) is approximately 94% effective in preventing pulmonary embolism (PE) or recurrent DVT. The routine placement of IVC filters in addition to anticoagulation in patients with documented DVT was investigated by Decousus et al. in a randomized trial. Decousus H, Leizorovicz A, Parent F, et al. A clinical trial of vena caval filters in the prevention of pulmonary embolism in patients with proximal deep-vein thrombosis. *N Engl J Med* 1998;338:409-415. This study revealed that the use of a permanent filter in addition to heparin therapy significantly decreased the occurrence of PE within the first 12 days compared to those without a filter. However, no effect was observed on either immediate or long-term mortality, and by 2 years, the initial benefit seen in the group of patients with filters was offset by a significant increase in the rate of recurrent DVT.

Despite the efficacy of anticoagulant therapy in the management of VTE, there are certain situations and conditions in which the benefits of anticoagulation are outweighed by the risks of instituting such a therapy. These include contraindications and complications of anticoagulant therapy. In such circumstances, there may be absolute or relative indications for filter insertion Currently, there are at least eleven types of permanent cava filters that are FDA approved. These include the Bird's Nest filter (Cook Incorporated, Bloomington, Ind.), Vena Tech LGM filter (B. Braun, Bethlehem Pa.), Vena Tech LP (B. Braun), Simon Nitinol filter (Bard, Covington, Ga.), Titanium Greenfield filter (Boston Scientific, Natick Mass.), Over-the-Wire Greenfield filter (Boston Scientific), TrapEase filter (Cordis Corp.), the Günther Tulip filter (Cook Inc.), the Cook Celect filter, the Bard Eclipse filter, and the Bard G2X filter.

Well-founded concerns over the long-term complications of permanent IVC filters, particularly in younger patients in need of PE prophylaxis with a temporary contraindication to anticoagulation, has led to the development of temporary and retrievable filters. Temporary filters remain attached to an accessible transcutaneous catheter or wire. These have been used primarily in Europe for PE prophylaxis during thrombolytic therapy for DVT. Currently these devices are not approved for use in the United States. Retrievable filters are very similar in appearance to permanent filters, but with modifications to the caval attachment sites and/or hooks at one end that can facilitate their removal. Retrievable filters that are currently available in the United States include the GÜNTHER TULIP or CELECT Filter (Cook Inc.), OPT EASE (Cordis Corp.), and RECOVERY, G2X or ECLIPSE nitinol filters (Bard Peripheral Vascular, Tempe, Ariz.). The time limit of retrievability is in part dependant on the rate of endothelialization of the device, which typically occurs within 2 weeks. However, differences in design may extend the time period in which the filter may be safely retrieved.

Currently no consensus exists as to which patients have an indication for a retrievable filter. However, it is generally accepted that patients at high risk for pulmonary embolism or with documented PE and with a temporary contraindication to anticoagulation are candidates.

Certain circumstances preclude the placement of a filter in the infrarenal IVC. This includes thrombus extending into the infrarenal IVC, renal vein thrombosis or pregnancy. The safety of suprarenal placement of IVC filters is well documented, with no reported instances of renal dysfunction and no differences in the rates of filter migration, recurrent PE or caval thrombosis.

The rate of upper extremity DVT is on the rise. This is predominantly due to an increasing number of patients having short- and long-term upper extremity central venous access catheters. In one study, 88% of patients found to have an upper extremity DVT had a central venous catheter present at the site of thrombosis at the time of diagnosis or within the previous two weeks. Pulmonary embolism may complicate upper extremity DVT in 12-16% of cases. In patients who have such a complication or contraindication to anticoagulation, a filter can be safely placed immediately below the confluence of the brachiocephalic veins. However, misplacement of an SVC filter is theoretically more likely than with an IVC filter because of the relatively short target area for deployment.

The most common imaging modality used for filter insertion is fluoroscopy, performed either in an interventional suite or an operating room. Bedside placement of filters has inherent advantages, particularly for critically ill patients in intensive care settings where transport can be avoided. Portable fluoroscopy, surface duplex ultrasound and intravascular ultrasound (IVUS) have all been used to assist with bedside filter placement.

Vena cava filter placement frequently occurs concomitantly with central access line placement or in critically ill patients that already have a central access line in place. Heretofore, however, there have been no devices which combine the function of a central access catheter and a removable vena cava filter.

One issue with all vascular filters is the problem of captured clot management. Captured clots raise a risk of total caval occlusion and patient death. Thus, reduction of clot size prior to filter removal or complete thrombolysis of the clot is necessary to restore caval flow patency. Similarly, where a vena cava filter is significantly occluded with clots, removal may be the primary and desired manner of clot management. During filter removal, any captured thrombus is typically squeezed by the contracting structural members of the vena cava filter. The pressure exerted by the vena cava filter on the clot may result in extrusion and or fragmentation of the clot material through the vena cava filter and into the distal blood flow. The attendant risk to the patient of clot material passing through the vena cava filter may be reduced by providing further distal or secondary protection to capture thrombus which is released from the vena cava filter as it is being collapsed and removed.

One particular type of vena cava filter is particularly well suited for use as distal or secondary protection. The BIRD'S NEST FILTER (Cook Medical, Inc., Indianapolis, Indiana) ("BNF") has some properties which are particularly useful as either secondary distal protection for primary vena cava filter removal or as a vena cava filter suitable for delivery through an already placed central line catheter. The BNF is constructed of a network of four biocompatible stainless steel wires. Each wire is 25 cm long and 0.18 mm in diameter. The wires are preshaped with many non-matching bends of a short radius. The wires are fixed at each end to V-shaped struts, the two legs of which are connected at a junction at an acute angle. A hook with a small loop stop minimizes the risk of IVC perforation at the end of each strut.

When a BNF is deployed, one of the V-shaped paired struts is pushed gently to engage to the IVC wall. Originally, it was recommended that the catheter be withdrawn by 1-3 cm over the pusher wire after the hooks were fixed to the IVC; later, it was recommended that 2 or 3 twists of 360° be applied. The purpose of the twists is to prevent or reduce the chance of wire prolapse. The second pair of struts is then pushed into the IVC so that the junctions overlap by 1-2 cm. The handle of the pusher wire is turned counterclockwise 10-15 times to free it from the struts.

Another wire-type filter is the SAFEFLO vena cava filter (Rafael Medical Technologies). The SAFEFLO vena cava filter, which is described in U.S. Pat. No. 6,482,222 consists of a single continuous wire member having a pre-set expanded shape consisting of plural substantially co-planar radially extending petals and plural ring structures about the circumference of the petals.

A particularly advantageous aspect of the BNF which lends itself to use with the present invention lies in the BNF's use of a network of biocompatible wires which are each pre-shaped with non-matching short radius bends that, upon deployment, form a highly tortuous network of wires which traverse the entire transverse cross-section of the inferior vena cava. Unlike the BNF, however, the present invention employs a conceptually similar, but structurally distinct, filter concept of a single pre-shaped wire or network of wires having a common longitudinal axis, which are deliverable through a lumen of a delivery catheter, such as a guidewire lumen, and upon existing a distal end of the delivery catheter lumen, the wire or network of wires assumes its pre-set shape, which may consist of non-matching short radius bends or other pre-set shapes that cause the wire or network of wires to bend in a manner that traverses across the entire transverse cross-section of the inferior vena cava.

SUMMARY OF THE INVENTION

The inventive filter may be utilized as either a stand-alone vena cava filter on either a temporary or permanent basis, or may be utilized as a secondary or salvage filter in conjunction with a primary vena cava filter such as that described in commonly assigned and co-pending U.S. patent application Ser. No. 12/684,839 filed Jan. 8, 2010, which is a continuation-in-part of U.S. patent application Ser. No. 11/849,225, filed Aug. 31, 2007, both of which are hereby incorporated by reference in their entireties herein.

In one aspect of the present invention, a vena cava filter catheter includes a catheter having a lumen disposed therethrough and at least one strand of biocompatible wire. The at least one strand has a first state in which the at least one strand has an elongate geometry suitable for traversing the lumen of the catheter and a second state in which the at least one strand assumes a pre-set geometry in which the at least one strand assumes a tortuous configuration adapted to occupy a space approximating a luminal diameter of an inferior vena cava.

In another aspect of the present invention, a vena cava filter catheter includes a catheter having at least one lumen disposed therethrough, a collapsible filter disposed on an exterior surface of the catheter, and at least one strand of biocompatible wire. The at least one strand has a first state in which the at least one strand has an elongate geometry suitable for traversing the at least one lumen of the catheter and a second state in which the at least one strand assumes a pre-set geometry in which the at least one strand assumes a tortuous configuration adapted to occupy a space approximating a luminal diameter of an inferior vena cava.

In a further aspect of the present invention, a method for implementing a vena cava filter catheter is presented. The vena cava filter catheter includes a catheter having at least one lumen disposed therethrough. The method comprises the steps of advancing at least one strand of a biocompatible wire in a first state having an elongate geometry through the at least one lumen of the catheter and pushing the at least one strand out of the catheter through an opening therein such that the at least one strand deploys to a second state having a tortuous configuration adapted to occupy a space approximating a luminal diameter of an inferior vena cava.

BRIEF DESCRIPTION OF THE DRAWINGS

The foregoing and other features and advantages of the invention are apparent from the following detailed description of exemplary embodiments, read in conjunction with the accompanying drawings, wherein like structural or functional elements are designated by like reference numerals.

DETAILED DESCRIPTION OF THE PREFERRED EMBODIMENTS

Figure 1A:
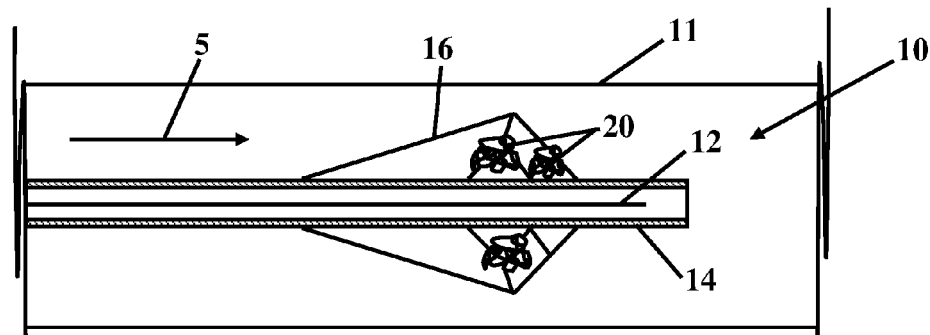
FIG. 1A is a diagrammatic side elevational view of a primary vena cava filter with captured thrombus.

Turning to the accompanying Figures, in which like structural or functional elements are designated by like reference numerals, the present invention consists generally of at least one biocompatible wire which has two geometric states, a first state in which the at least one biocompatible wire has an elongate linear geometry suitable for traversing a lumen of a delivery catheter, and a second state in which the at least one biocompatible wire assumes a pre-set geometry in which the at least one wire assumes a convoluted and highly tortuous configuration to occupy a space approximating the luminal diameter of an inferior vena cava. The first state is suitable for both delivery and retrieval of the at least one biocompatible wire, while the second state exists when the at least one biocompatible wire is pushed from a distal end of a delivery catheter lumen, is unconstrained, and deployed to assume its pre-set shape.

Figure 1B:
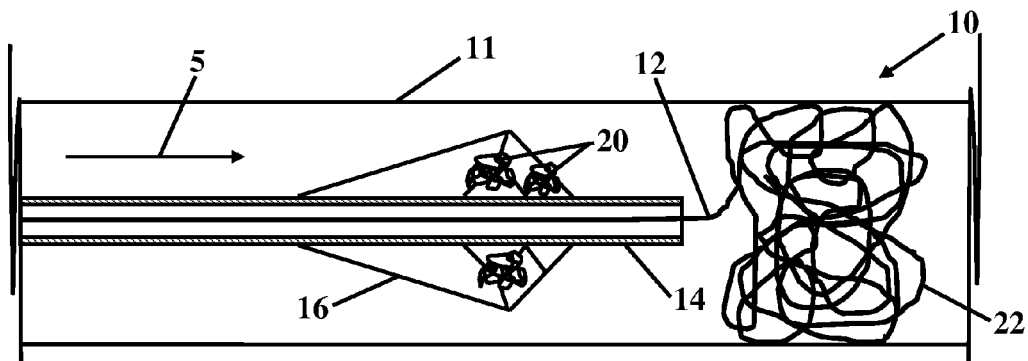
FIG. 1B is a side diagrammatic side elevational view of the primary vena cava filter with captured thrombus with a secondary vena cava filter introduced and deployed through a central lumen of a catheter carrying the primary vena cava filter.
Figure 1C:
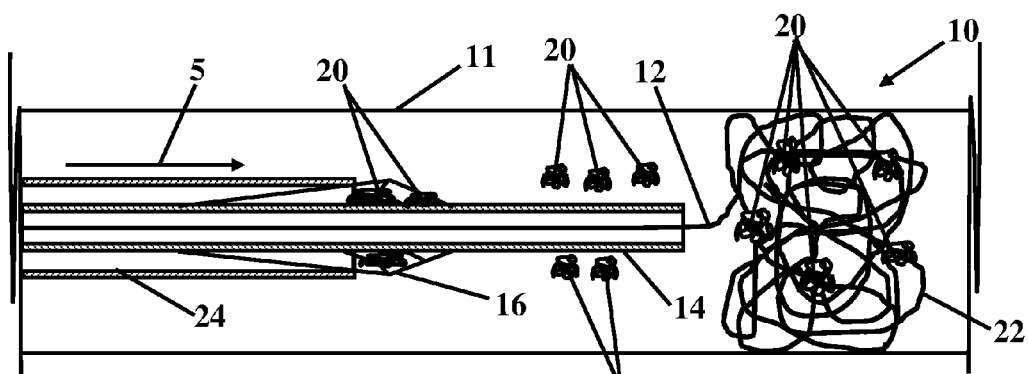
FIG. 1C is a diagrammatic side elevational view of a primary vena cava filter being withdrawn after deployment of a secondary vena cava filter and thrombus being released from the primary vena cava filter and captured by the secondary vena cava filter.
Figure 5:
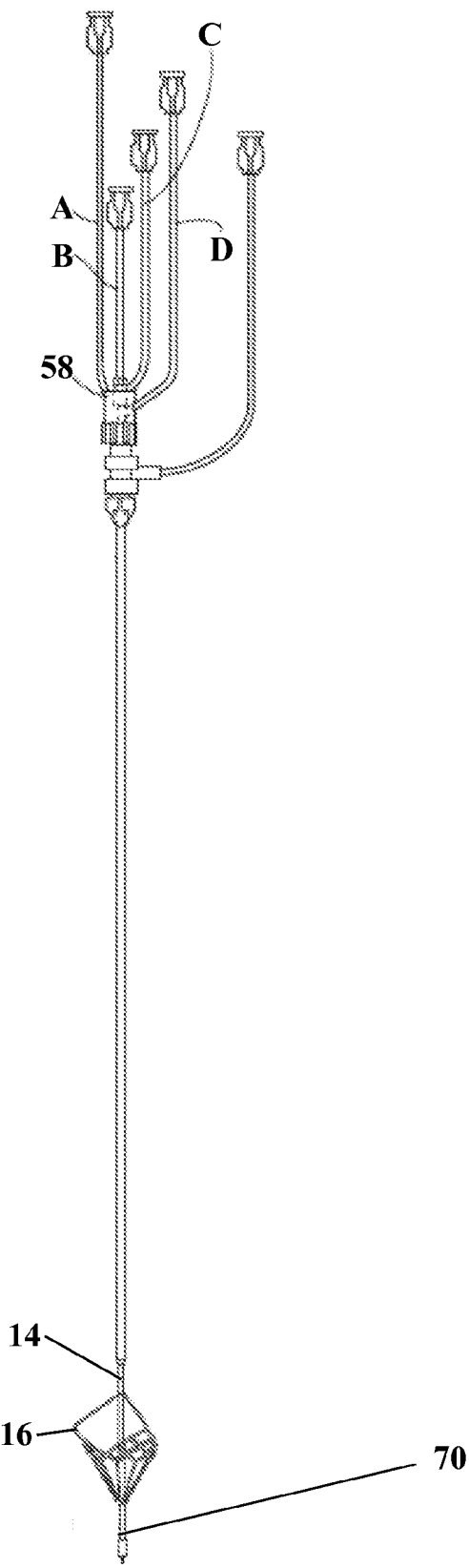
FIG. 5 is a plan view of an embodiment of a vena cava filter catheter.

FIGS. 1A to 1C depict serial diagrammatic views of an embodiment of the inventive vena cava filter system 10 that employs an inventive filter 12 as a secondary or salvage filter to assist in the clot capture upon removal of a primary filter 16. After the primary filter 16 has been deployed within an inferior vena cava 11 and has captured thrombus 20 therein, the secondary filter 12 is delivered through a lumen of the catheter 14, which may comprise a central line catheter as disclosed in co-pending U.S. patent application Ser. No. 12/684,839 filed Jan. 8, 2010 and co-pending U.S. patent application Ser. No. 11/849,225 filed Aug. 31, 2007. Referring to FIG. 5, originally appearing in U.S patent application Ser. No. 12/684,839 filed Jan. 8, 2010, a lumen in the catheter 14 may be in fluid communication with one or more of a plurality of fluid lines A, B, C, D via a proximal hub member 58. The elongate linear at least one biocompatible wire making up the filter 12 is well-suited to being introduced, for example, through the proximal hub member 58 and pushed distally through an appropriately dimensioned lumen in the catheter 14 until it exits the catheter 14 for deployment. As discussed further hereinbelow, in such a configuration, a proximal end of the filter 12 is accessible at the proximal hub member 58 and/or via one or more of the fluid lines A, B, C, D.

The filter 12 may exit a distal end of the catheter 14 for distal deployment or, where a multi-lumen catheter 14 is employed, the catheter 14 may have an opening proximal the distal end to permit more proximal deployment of the filter 12, such as opening 70 in FIG. 5. Once the filter 12 exits the catheter 14, the filter 12 assumes its second state 22 in which it becomes highly convoluted and enlarges to engage the entire diameter of the inferior vena cava 11. The highly convoluted and tortuous windings of the secondary filter 12 create multiple regions in the filter 12 for thrombus capture. Vector arrow 5 represents the directional blood flow through the blood vessel 11.

Once deployed, secondary filter 12 is positioned distal, relative to the blood flow through the inferior vena cava, to the primary filter 16. Once the secondary filter 12 is fully deployed, as depicted in FIG. 1B, a capture sheath 24 may be placed concentrically over the catheter 14 and the catheter 14 withdrawn into the capture sheath 24 to collapse the primary filter 16. During capture of the primary filter 16, thrombus 20 captured in the primary filter 16 may become dislodged or extruded from the primary filter 16 into the blood flow 5 and travel distal to the primary filter 16. Thrombus 20 released from the primary filter 16 will become captured by the secondary filter 12 and may be treated by thrombolysis or other appropriate therapeutic modality.

While not specifically illustrated, it will be understood by those skilled in the art that the filter 12 may be employed as a primary filter, on either a permanent or temporary basis, and the catheter 14 may be a delivery catheter for delivering and deploying the filter 12 or, alternatively, the catheter 14 may be a central line catheter through which the filter 12 is delivered and deployed, or, alternatively, the catheter 14 may be a central line catheter having a primary filter 16 thereupon as described in the patent applications incorporated by reference.

Figure 2:
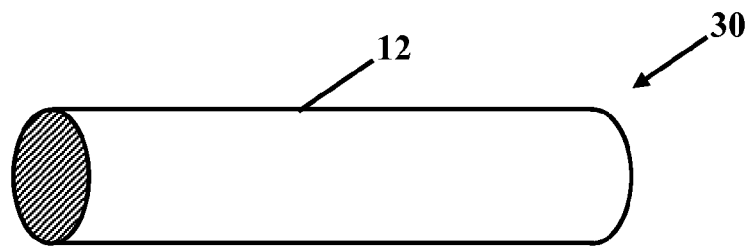
FIG. 2 is a side elevational view of an illustrative segment of a secondary vena cava filter illustrating its construction as a solid wire member.
Figure 3:
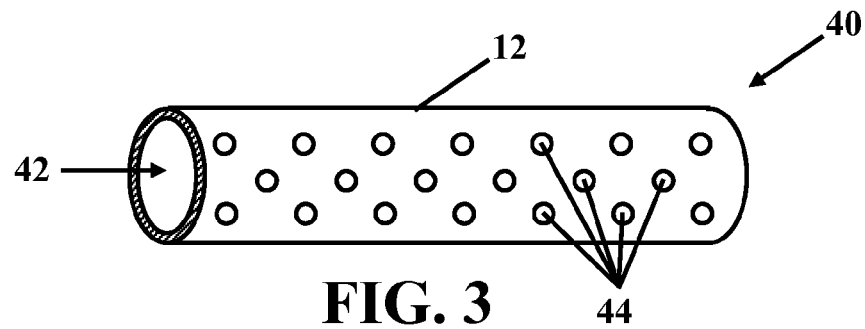
FIG. 3 is a side elevational view of an illustrative segment of an alternative embodiment of a second vena cava filter illustrating its construction as a tubular member.

FIGS. 2 and 3 depict alternative embodiments of the filter 12. As illustrated in FIG. 2, the filter 12 consists of at least one strand of solid biocompatible wire 30. The at least one strand of solid biocompatible wire 30 have a cylindrical shape as illustrated with a generally circular transverse cross-sectional shape, may have other curvilinear shapes such as an elliptical or oval transverse shape, or may have a polygonal cross-sectional shape, such as a quadrilateral, pentagonal, hexagonal or other suitable solid shapes.

As illustrated in FIG. 3, the filter 12 may consist of at least one strand of a hollow biocompatible wire 40 having an inner lumen 42 and a plurality of openings 44 passing through the hollow biocompatible wire 40 and communicating between the lumen 42 and external the wire 40. The plurality of openings 44 may be patterned randomly about a length and circumference of the wire 40 or may be provided only on certain longitudinal regions of the wire 40 or only on certain circumferential regions of the wire. Further, the plurality of openings 44 may have different angular orientations through walls of the wire 40, i.e., other than perpendicular to the luminal and exterior wall of the wire 40. A fluid, such as a biologically active agent, e.g., a thrombolytic, may be introduced through the lumen 42 of the wire 40 and be expelled through the plurality of openings 44 to shower thrombus captured in the filter 12 with the biologically active agent.

As noted hereinabove in regard to FIG. 5, the proximal end of the filter 12, in one embodiment, may be accessible at the proximal hub member 58 and/or via one of the fluid lines A, B, C, D. The proximal end of the filter 12 may be affixed or anchored within the proximal hub member 58 and/or within one or more of the fluid lines A, B, C, D. Such arrangement facilitates fluid communication between the lumen 42 of the hollow biocompatible wire 40 and the one or more of the fluid lines A, B, C, D to facilitate control over the delivery of a biologically active agent through the lumen 42. Such arrangement also facilitates the introduction of a secondary catheter (not shown) that may be tracked over the filter 12 to retrieve the filter 12 in the event that the primary catheter 14 was removed, for example, for patient comfort as discussed hereinbelow.

The variants of position and angular orientation of the plurality of openings 44 permit directional control over the flow of the fluid as it passes through the plurality of openings 44 and out of the wire 40. Like solid biocompatible wire 30, hollow biocompatible wire 40 may have a cylindrical shape as illustrated with a generally circular transverse cross-sectional shape, may have other curvilinear shapes such as an elliptical or oval transverse shape, or may have a polygonal cross-sectional shape, such as a quadrilateral, pentagonal, hexagonal or other suitable hollow shapes.

Where the filter 12 is to be placed for extended periods of time, it may be desirable to remove proximally extending sections of the catheter 14 or the filter 12 for patient comfort and/or to reduce the likelihood of inadvertent removal of the filter 12 or the catheter 14 from the patient. In this circumstance, it is desirable to employ a means for anchoring the filter 12 within the catheter 14 and a means for retrieving the filter 12 from the catheter 14 to ensure that the filter 12 may be withdrawn from the patient.

Figure 4:
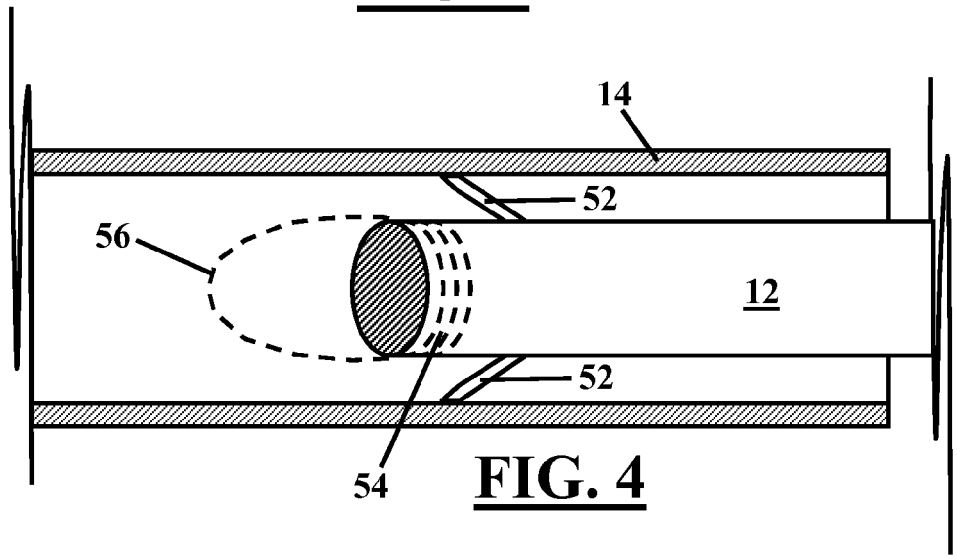
FIG. 4 is a diagrammatic side elevational view of a secondary vena cava filter and alternative embodiments for anchoring the secondary vena cava filter within a central line catheter and for releasing or retrieval of the secondary vena cava filter after withdrawal of delivery apparatus.

As illustrated in FIG. 4, and in accordance with one embodiment of the invention, the means for anchoring the filter 12 may consist of one or more barbs 52 which project outwardly from a central longitudinal axis of the filter 12. The one or more barbs 52 may engage with inner walls of a lumen of the catheter 14, with inner walls of the proximal hub member 58, or with inner walls of one of the plurality of fluid lines A, B, C, D to retain the filter 12 in a fixed position relative to the lumen of the catheter 14. Alternative structures for anchoring the filter 12 relative to any of the above-noted inner walls are envisioned by the present invention and may, for example, include expandable ring-like structures, expandable leaf-like structures, an expandable balloon, expandable coil structures, or the like which provide an enlarged sections of the filter 12 to positionally retain the filter 12 against any of the above-noted inner walls.

Anchoring or fixation of the proximal end of the filter 12 relative to the proximal hub 58 such that the lumen 42 of the hollow biocompatible wire 40 is exclusively accessible by one of the plurality of fluid lines A, B, C, D facilitates the infusion of a biologically active agent through the lumen 42. Further, it is contemplated that such anchoring may facilitate a sealed access to the lumen 42 via one or more of the plurality of fluid lines A, B, C, D and that such sealed access facilitates the infusion of the biologically active agent at a pressure that is higher than would be possible without sealed access. For example, sealed access could be achieved by connection via luer fitting or other type of fitting as known in the art of the proximal end of the hollow biocompatible wire 40 to one of the plurality of fluid lines A, B, C, D, or to an external fluid line (not shown) that is introduced via one of the fluid lines A, B, C, D.

Also as illustrated in FIG. 4, and in accordance with one embodiment of the invention, the means for retrieving the filter 12 may consist of a loop 56 on an end of the filter 12 which may be used as a snare for capturing the filter 12. Alternatively, the end of the filter 12 may be provided with threads 54 or other mechanical or physical linkages, such as a detent ring, detent nipple, magnet or other mechanical or physical interface by which an external member may mechanically or physically engage the end of the filter 12 for retrieval of the filter 12 from the patient.

Figure 6:
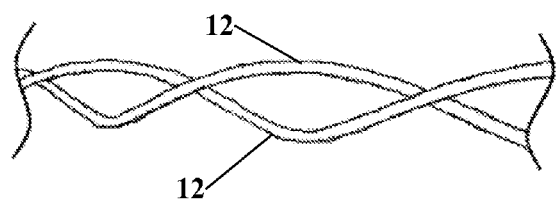
FIG. 6 is a partial view of an illustrative segment of an alternative embodiment of a second vena cava filter illustrating its construction as a plurality of helically wound wire members.
Figure 7:
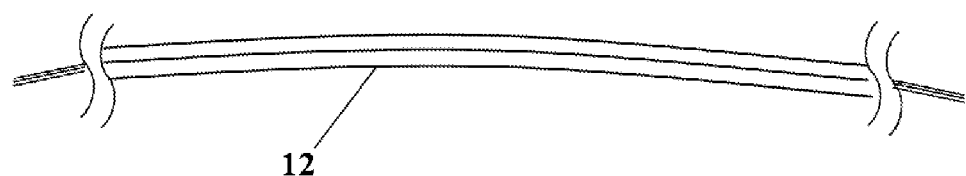
FIG. 7 is a partial view of an illustrative segment of an alternative embodiment of a second vena cava filter illustrating its construction as a plurality of adjacent wire members joined at proximal and distal ends.

Finally, while the invention has been described with reference to at least one biocompatible wire member 12, it should be understood that the invention contemplates a filter 12 made of plural biocompatible wire members which may be helically wound about each other where the wound wire is pre-set to a single shape, as shown in FIG. 6. Alternatively, the plural biocompatible wires may be joined at proximal and distal ends and laid adjacent one another in either a ribbon-like structure, as shown in FIG. 7, or as a bundle where each wire strand is free to assume its individual pre-set shape or as a collective pre-set shape.

An inventive filter that may be utilized as either a stand-alone vena cava filter on either a temporary or permanent basis, or may be utilized as a secondary or salvage filter in conjunction with a primary vena cava filter is presented.

It will be appreciated by those skilled in the art that changes could be made to the embodiments described hereinabove without departing from the broad concepts disclosed therein. For example, while the present invention has been described with reference to its preferred embodiments, those of ordinary skill in the art will understand that variations in material selection, device geometry, dimensions, and intended usage may be made without departing from the scope of the present invention. It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the vena cava filter catheter described herein and to teach the best mode of carrying out the same.

What is claimed is:

1. A vena cava filter catheter, comprising:
   a. a catheter having at least one lumen disposed therethrough;
   b. a collapsible vena cava filter disposed about a distal portion of the catheter, such that the collapsible vena cava filter is disposed proximal from an opening associated with the at least one lumen; and
   c. at least one strand of biocompatible wire having a first state in which the at least one strand has an elongate geometry suitable for traversing the at least one lumen of the catheter and exiting from the opening, and having a second state in which the at least one strand assumes a pre-set geometry in which the at least one strand assumes a tortuous configuration adapted to occupy a space approximating a luminal diameter of an inferior vena cava.

2. The vena cava filter catheter of claim 1, further comprising a capture sheath disposed over the catheter such that withdrawal of the catheter into the capture sheath collapses the collapsible filter within the capture sheath.

3. The vena cava filter catheter of claim 2, wherein the at least one strand of biocompatible wire comprises at least one strand of hollow biocompatible wire having an interior lumen and a plurality of openings disposed through a wall of the hollow biocompatible wire to provide fluid communication between the interior lumen and external to the hollow biocompatible wire.

4. The vena cava filter catheter of claim 3, further including a biologically active agent adapted to be delivered through the interior lumen to shower thrombus captured within the at least one strand deployed to the second state.

5. The vena cava filter catheter of claim 1, wherein the catheter has a plurality of lumens disposed therethrough and wherein the at least one lumen has an opening proximal to a distal end of the catheter and distal the collapsible vena cava filter.

6. The vena cava filter catheter of claim 1, wherein the at least one strand of biocompatible wire comprises at least one strand of solid biocompatible wire.

7. The vena cava filter catheter of claim 1, wherein the at least one strand of biocompatible wire has a cross-sectional shape selected from the group of cross-sectional shapes consisting of: generally circular; elliptical; oval; regular polygonal; and irregular polygonal.

8. The vena cava filter catheter of claim 1, wherein the at least one strand of biocompatible wire comprises a plurality of strands of biocompatible wires.

9. The vena cava filter catheter of claim 8, wherein the plurality of strands of biocompatible wires is helically wound around one another in the first state.

10. The vena cava filter catheter of claim 8, wherein the plurality of strands of biocompatible wires is joined at proximal and distal ends and laid adjacent one another in the first state.

11. The vena cava filter catheter of claim 1, further comprising one or more barbs projecting outwardly from a central longitudinal axis of the at least one strand of biocompatible wire in the second state.

12. The vena cava filter catheter of claim 11, wherein the one or more barbs are adapted to engage with inner walls of the at least one lumen of the catheter, inner walls of a proximal hub in fluid communication with the catheter, or inner walls of a fluid line in fluid communication with the proximal hub to facilitate anchoring of the at least one strand in the second state in a fixed position relative to the lumen.

13. The vena cava filter catheter of claim 1, further comprising a loop on a proximal end of the at least one strand of biocompatible wire, wherein the loop is adapted to be used as a snare for capturing the at least one strand of biocompatible wire.

14. A method for implementing a vena cava filter catheter, wherein the vena cava filter catheter includes a catheter having at least one lumen disposed therethrough, a collapsible vena cava filter disposed about a distal portion of the catheter, such that the collapsible vena cava filter is disposed proximal from an opening associated with the at least one lumen, and at least one strand of biocompatible wire having a first state in which the at least one strand has an elongate geometry suitable for traversing the at least one lumen of the catheter and exiting from the opening, and having a second state in which the at least one strand assumes a pre-set geometry in which the at least one strand assumes a tortuous configuration adapted to occupy a space approximating a luminal diameter of an inferior vena cava, the method comprising the steps of:
  a. advancing the at least one strand of biocompatible wire in the first state having an elongate geometry through the at least one lumen of the catheter;
  b. pushing the at least one strand out of the catheter through an opening therein such that the at least one strand deploys to the second state having a tortuous configuration adapted to occupy a space approximating a luminal diameter of an inferior vena cava.

15. The method of claim 14, wherein the at least one strand of biocompatible wire comprises at least one strand of hollow biocompatible wire having an interior lumen and a plurality of openings disposed through a wall of the hollow biocompatible wire to provide fluid communication between the interior lumen and external to the hollow biocompatible wire, and further comprising the step of introducing a biologically active agent through the interior lumen to shower thrombus captured within the at least one strand deployed to the second state with the biologically active agent.

16. The method of claim 14, wherein a capture sheath is disposed over the catheter, and further comprising the step of withdrawing the catheter into the capture sheath such that the collapsible filter collapses within the capture sheath.

17. The method of claim 14, further comprising one or more barbs projecting outwardly from a central longitudinal axis of the at least one strand in the second state and adapted to engage with inner walls of the at least one lumen to facilitate anchoring of the at least one strand in the second state in a fixed position relative to the at least one lumen, and further comprising the step of anchoring the at least one strand to the at least one lumen with the one or more barbs.

18. The method of claim 17, further comprising a retrieval interface disposed on a proximal end of the at least one strand, wherein the retrieval interface is selected from the group of retrieval interfaces consisting of: a loop; threads; a detent ring; a detent nipple; and a magnet; and further comprising the steps of: inserting a capture member having a distal end that is adapted to capture the retrieval interface through the at least one lumen of the catheter; and capturing the retrieval interface with the capture member.

* * * * *